US007786442B2

(12) United States Patent
Norling et al.

(10) Patent No.: US 7,786,442 B2
(45) Date of Patent: Aug. 31, 2010

(54) METHOD AND APPARATUS FOR ION SOURCE POSITIONING AND ADJUSTMENT

(75) Inventors: Jonas Ove Norling, Uppsala (SE); Jan-Olof Bergström, Uppsala (SE)

(73) Assignee: General Electric Company, Schenectady, NY (US)

( * ) Notice: Subject to any disclaimer, the term of this patent is extended or adjusted under 35 U.S.C. 154(b) by 1811 days.

(21) Appl. No.: 10/869,879

(22) Filed: Jun. 18, 2004

(65) Prior Publication Data

US 2005/0283199 A1 Dec. 22, 2005

(51) Int. Cl.
*A61N 1/24* (2006.01)

(52) U.S. Cl. .................................................. 250/363.03

(58) Field of Classification Search ............ 250/363.03, 250/341.1, 393, 492.21, 424, 492.3, 427, 250/423 R; 315/502; 313/62
See application file for complete search history.

(56) References Cited

U.S. PATENT DOCUMENTS 2,531,065 A 11/1950 Livingood et al.
3,714,423 A * 1/1973 Lucas .......................... 250/311
4,572,021 A * 2/1986 Guarracini et al. ....... 74/490.13
4,721,918 A 1/1988 Koudijs
5,497,060 A * 3/1996 Juergens, III ................ 700/60
5,763,986 A 6/1998 Nakanishi et al.
7,038,403 B2 * 5/2006 Mastrangeli et al. ......... 315/502
2004/0217530 A1 * 11/2004 Harris et al. .................. 269/55
2005/0127927 A1 * 6/2005 Harris et al. ................ 324/754

FOREIGN PATENT DOCUMENTS

EP 0 769 891 4/1997

OTHER PUBLICATIONS

Milton, B.F., "Design of an Axial Injection System for the Seattle MC50 Cyclotron", Cyclotrons and Their Applications—Proceedings of the Fifteenth International Conference, IOP Publishing, Bristol, UK, pp. 638-641, XP002539492, (1999).
French Patent Office Preliminary Search Report for French Application No. 0506186, dated Jul. 31, 2009.

* cited by examiner

*Primary Examiner*—David P Porta
*Assistant Examiner*—Djura Malevic
(74) *Attorney, Agent, or Firm*—Hunton & Williams, LLP

(57) ABSTRACT

The invention is directed to a method and apparatus for ion source positioning and adjustment. According to one embodiment, the invention relates to an apparatus for ion source positioning and adjustment. The apparatus comprises a bottom plate, a middle plate and a top plate, wherein the top plate is coupled to the middle plate by at least one adjustment member for causing the top plate to move in a first direction, wherein the at least one adjustment member positions the top plate in a predetermined position with respect to the middle plate; and the middle plate is coupled to the bottom plate by a worm gear assembly for causing the middle plate to move in a second direction with respect to the bottom plate.

20 Claims, 7 Drawing Sheets

METHOD AND APPARATUS FOR ION SOURCE POSITIONING AND ADJUSTMENT

BACKGROUND OF THE INVENTION

The present invention relates generally to the field of cyclotron design for radiopharmacy and more particularly to a method and apparatus for ion source positioning and adjustment.

Hospitals and other health care providers rely extensively on positron emission tomography (PET) for diagnostic purposes. PET scanners can produce images which illustrate various biological process and functions. In a PET scan, the patient is initially injected with a radioactive substance known as a PET isotope (or radiopharmaceutical). The PET isotope may be $^{18}$F-fluoro-2-deoxyglucose (FDG), for example, a type of sugar which includes radioactive fluorine. The PET isotope becomes involved in certain bodily processes and functions, and its radioactive nature enables the PET scanner to produce an image which illuminates those functions and processes. For example, when FDG is injected, it may be metabolized by cancer cells, allowing the PET scanner to create an image illuminating the cancerous region.

PET isotopes are mainly produced with cyclotrons, a type of circular-shaped particle accelerators. FIG. 1 illustrates the operation of a known cyclotron for isotope production. The cyclotron comprises two hollow D-shaped metal electrodes 102 and 104 that are placed in a magnetic field B. The two electrodes 102 and 104 are separated by a small gap 103, across which an alternating electric field E is applied. The cyclotron usually operates at high vacuum (e.g., $10^{-7}$ Torr). In operation, a negative ion 108 is initially extracted from an ion source 106 near the center of the cyclotron. Confined by the magnetic field, the ion 108 starts moving in a circular path. A radio frequency (RF) high voltage source rapidly alternates the polarity of the electric field E, so that the ion 108 is accelerated each time it crosses the gap 103. As it acquires more kinetic energy, the ion 108 follows a spiral course 110 until it is eventually directed to a target material to produce desired PET isotopes.

FIG. 2 illustrates the operation of a known plasma-based ion source 200 used in cyclotrons for isotope production. As shown, the ion source 200 comprises an ion source tube 204 positioned between two cathodes 202. The ion source tube 204 may be grounded while the two cathodes 202 may be biased at a high negative potential with a power source 212. The ion source tube 204 may have a cavity 208 into which one or more gas ingredients may be flowed. For example, a hydrogen ($H_2$) gas of certain pressure may be flowed into the cavity 208. The voltage difference between the cathodes 202 and the ion source tube 104 may cause a plasma discharge 210 in the hydrogen gas, creating positive hydrogen ions (protons) and negative hydrogen ions ($H^-$). These hydrogen ions may be confined by a magnetic field 220 imposed along the length of the ion source tube 204. A puller 216, biased with a power source 214 at an alternating potential, may then extract the negative hydrogen ions through a slit opening 206 on the ion source tube 204. The extracted negative hydrogen ions 218 may be further accelerated in the cyclotron (not shown) before being used in isotope production.

Traditionally, after positioning and adjustment of the slit opening, the only way to determine whether the position is acceptable is by measuring the ion source output. In order to measure the ion source output, the cyclotron chamber has to be pumped down to an acceptable vacuum level. In one cyclotron, for example, it takes about an hour to reach such a vacuum level. If measurement of the ion source output reveals that the slit opening has not been accurately positioned, the cyclotron chamber has to be re-opened to allow re-adjustment. Unfortunately, a simple reading of the ion source output does not offer a clear indication as to which direction or by how much the ion source tube should be adjusted. A service engineer usually has to adjust the position in small increments and repeat the pump-and-measure process for several times until a desired ion source output is measured. One iteration can take 2-3 hours. For an inexperience service engineer, it may take several iterations to achieve an acceptable level of ion source output. Therefore, the traditional approach for ion source positioning and adjustment can be very time-consuming. Even when an acceptable level of ion source output has been achieved, it is seldom clear whether an optimal position of the ion source tube has been reached.

Unfortunately, ion source adjustment is hardly avoidable since an ion source typically has a limited lifetime and requires periodical replacement. During a scheduled service, the cyclotron needs to be opened up to allow access to the ion source. However, since the cyclotron usually becomes radioactive during isotope production, it is necessary to wait for the radiation to decay to a safe level before starting the service. The wait for the radiation decay can sometimes last ten hours, for example. The safe level of radiation usually depends on how long a service engineer will be exposed. That is, a job that takes a short time can be started at a higher radiation level (i.e., after a shorter decay time) than one that takes a long time. Therefore, the shorter it takes to position and adjust a new ion source, the faster a scheduled service may be completed.

In view of the foregoing, it would be desirable to provide a more efficient solution for accurate positioning and adjustment of an ion source tube.

BRIEF SUMMARY OF THE INVENTION

The present invention is directed to a method and apparatus for ion source positioning and adjustment that overcomes drawbacks of known systems and methods.

According to one embodiment, the invention relates to an apparatus for ion source positioning and adjustment. The apparatus comprises a bottom plate, a middle plate and a top plate, wherein the top plate is coupled to the middle plate by at least one adjustment member for causing the top plate to move in a first direction, wherein the at least one adjustment member positions the top plate in a predetermined position with respect to the middle plate; and the middle plate is coupled to the bottom plate by a worm gear assembly for causing the middle plate to move in a second direction with respect to the bottom plate.

According to another embodiment, the invention relates to a method for ion source positioning and adjustment. The method comprises: coupling an ion source tube to a top plate of an adjustment tool, wherein the top plate is coupled to a middle plate by at least one adjustment member for causing the top plate to move in a first direction; installing the adjustment tool by attaching a bottom plate of the adjustment tool to a chamber of a cyclotron; adjusting the at least one adjustment member until the top plate is at a predetermined position with respect to the middle plate; and driving a worm gear that causes the middle plate to move in a second direction with respect to the bottom plate, until a desired output of the ion source tube is measured.

BRIEF DESCRIPTION OF THE DRAWINGS

In order to facilitate a fuller understanding of the present invention, reference is now made to the appended drawings.

These drawings should not be construed as limiting the present invention, but are intended to be exemplary only.

DETAILED DESCRIPTION OF THE INVENTION

Reference will now be made in detail to exemplary embodiments of the invention, examples of which are illustrated in the accompanying drawings.

Figure 1:
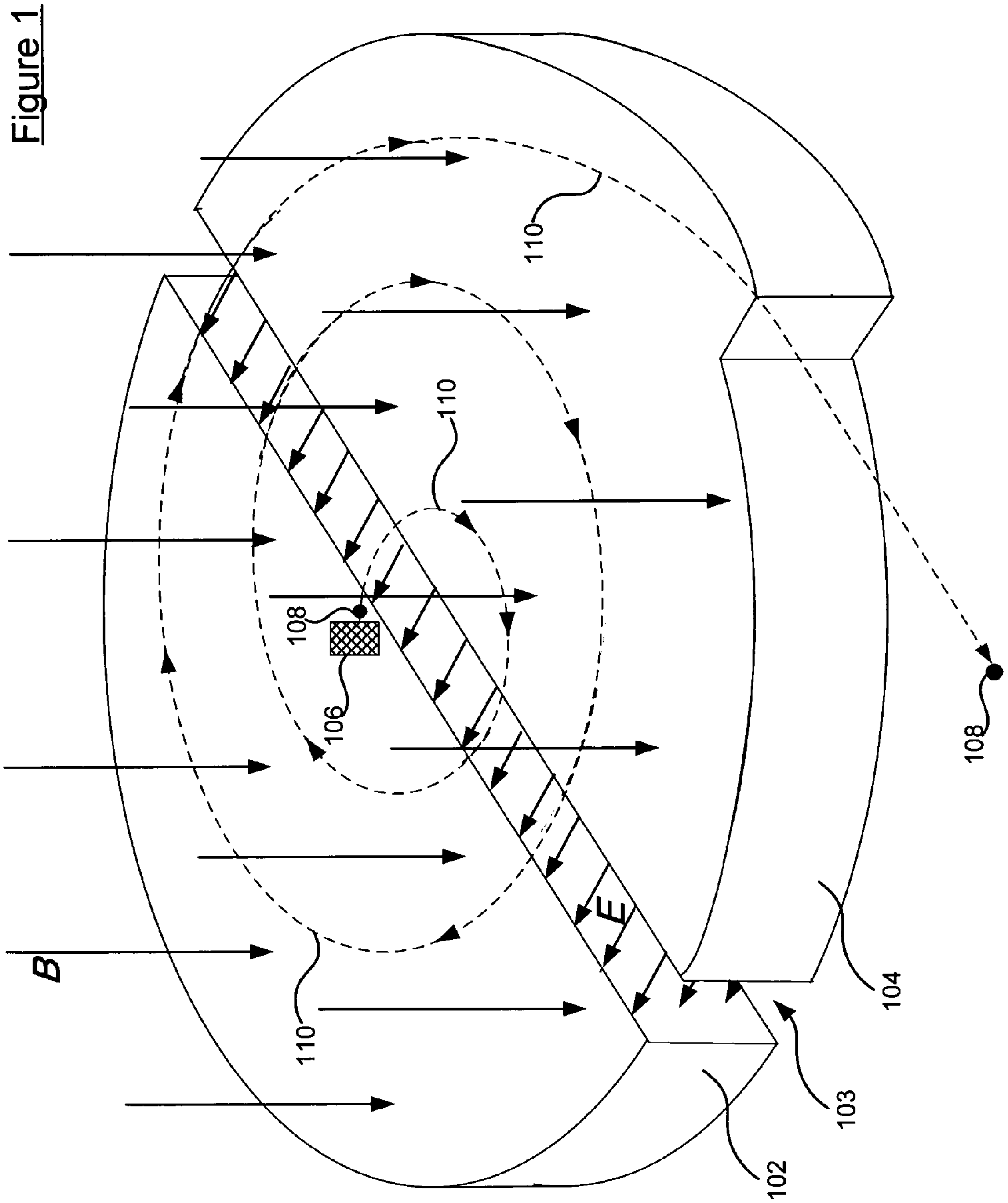
FIG. 1 illustrates the operation of a known cyclotron for isotope production.
Figure 2:
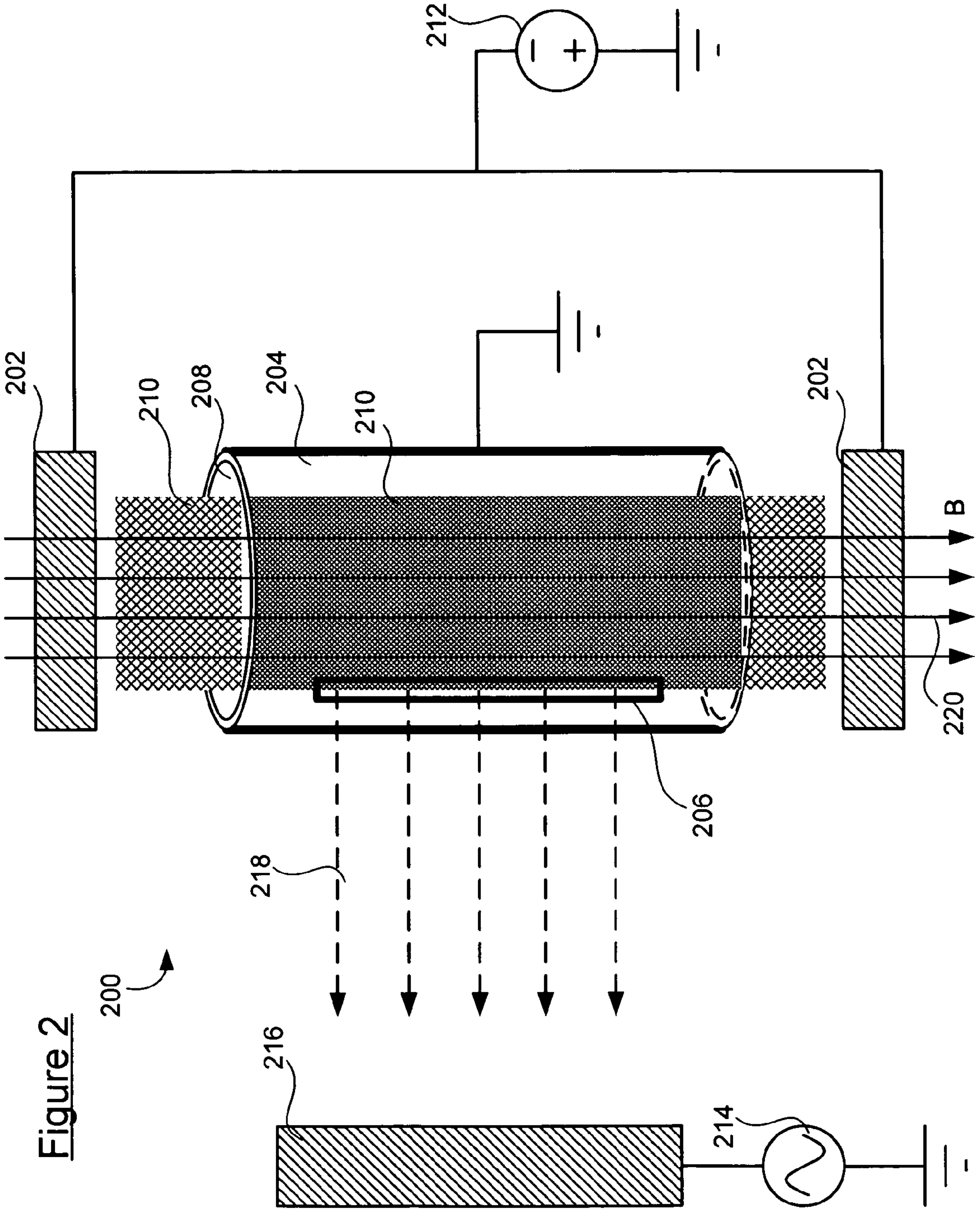
FIG. 2 illustrates the operation of a known plasma-based ion source used in cyclotrons for isotope production.

In an ion source similar to the one shown in FIG. 2, positioning of the slit opening relative to the puller is a significant factor affecting ion extraction. The position of the ion source tube usually has to be accurate within a fraction of a millimeter. Accurate positioning of the ion source tube usually depends on three parameters: its distance to the puller (or "longitudinal position"), the lateral position of the slit opening relative to the puller, and angle of the slit opening with respect to the ion source body. Of these three parameters, the lateral position of the slit opening is usually most significant. The distance to the puller and the lateral position may be accurately and efficiently adjusted based on the method and apparatus described hereinafter. The angle of the slit opening may be fixed easily by a special angle tool during installation of the ion source tube.

Figure 3:
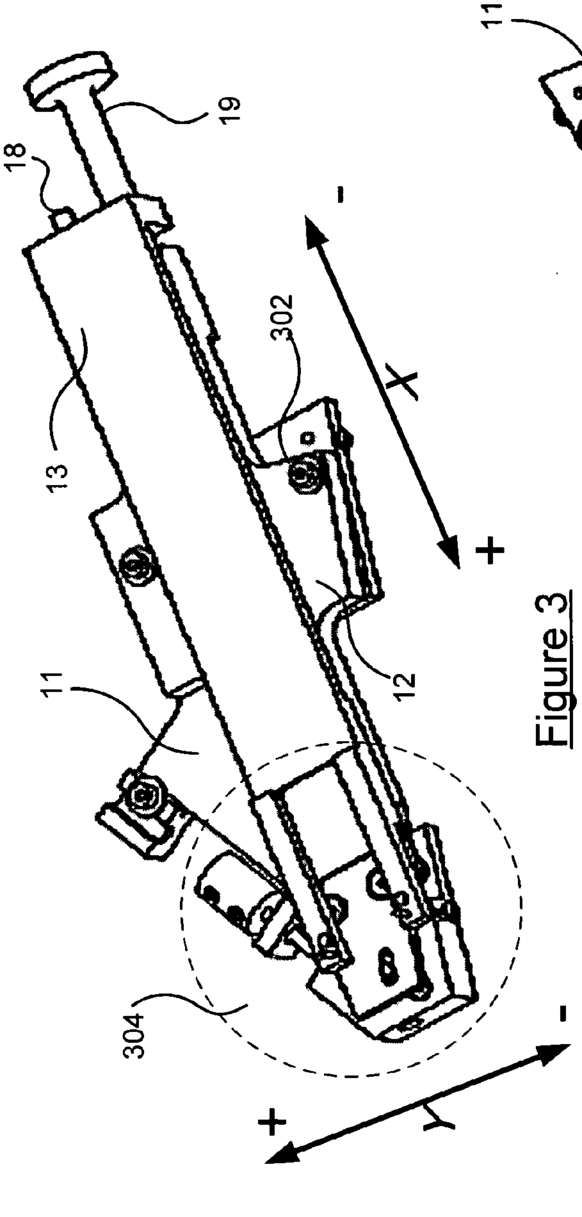
FIGS. 3 and 4 illustrate an exemplary ion source adjustment tool according to an embodiment of the invention.
Figure 4:
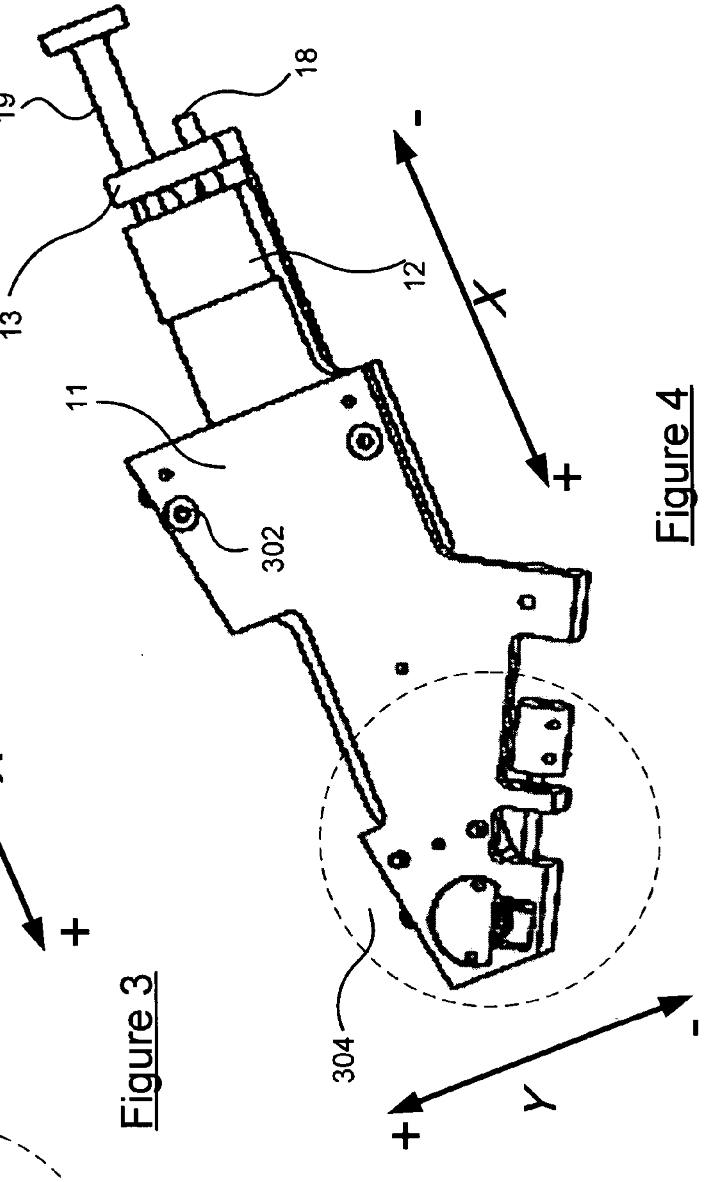

FIGS. 3 and 4 illustrate an exemplary ion source adjustment tool according to an embodiment of the invention. FIG. 3 shows the front side of the exemplary ion source adjustment tool, and FIG. 4 shows the back side.

The exemplary ion source adjustment tool may comprise three plates: a top plate 13, a middle plate 12, and a bottom plate 11. The top plate 13 may be coupled to the middle plate 12 by a knurled screw 19. The knurled screw 19 may go through the top plate 13 and into the middle plate 12, such that, when the knurled screw 19 is turned, the top plate 13 may slide back or forth with respect to the middle plate 12. Movement of the top plate 13 may be a linear movement along the ±X directions. A stop screw 18 placed next to the knurled screw 19 may control a relative position of the top plate 13 with respect to the middle plate 12. This relative position may vary for different cyclotrons. The stop screw 18 may go through the top plate 13 and may act as a stop when it touches a back part of the middle plate 12. The stop screw 18 may be adjusted to control how far it extends to touch the middle plate 12. Apart from the combination of a knurled screw and a stop screw, other mechanisms known in the art may also be used to control the relative position of the top plate 13 with respect to the middle plate 12. For example, a single knurled screw may be used, together with markings along the edges of top plate 13 and/or the middle plate 12, to adjust the relative position.

The middle plate 12 may be coupled to the bottom plate 11 by a worm gear assembly 304. The worm gear assembly 304 may cause the middle plate 12 to rotate slightly around a pivot 302. The rotation is typically so small that the tip of the middle plate 12 can be viewed as moving along the ±Y directions. Details of the worm gear assembly 304 and its operation will be described in connection with FIGS. 6 and 7.

Figure 5:
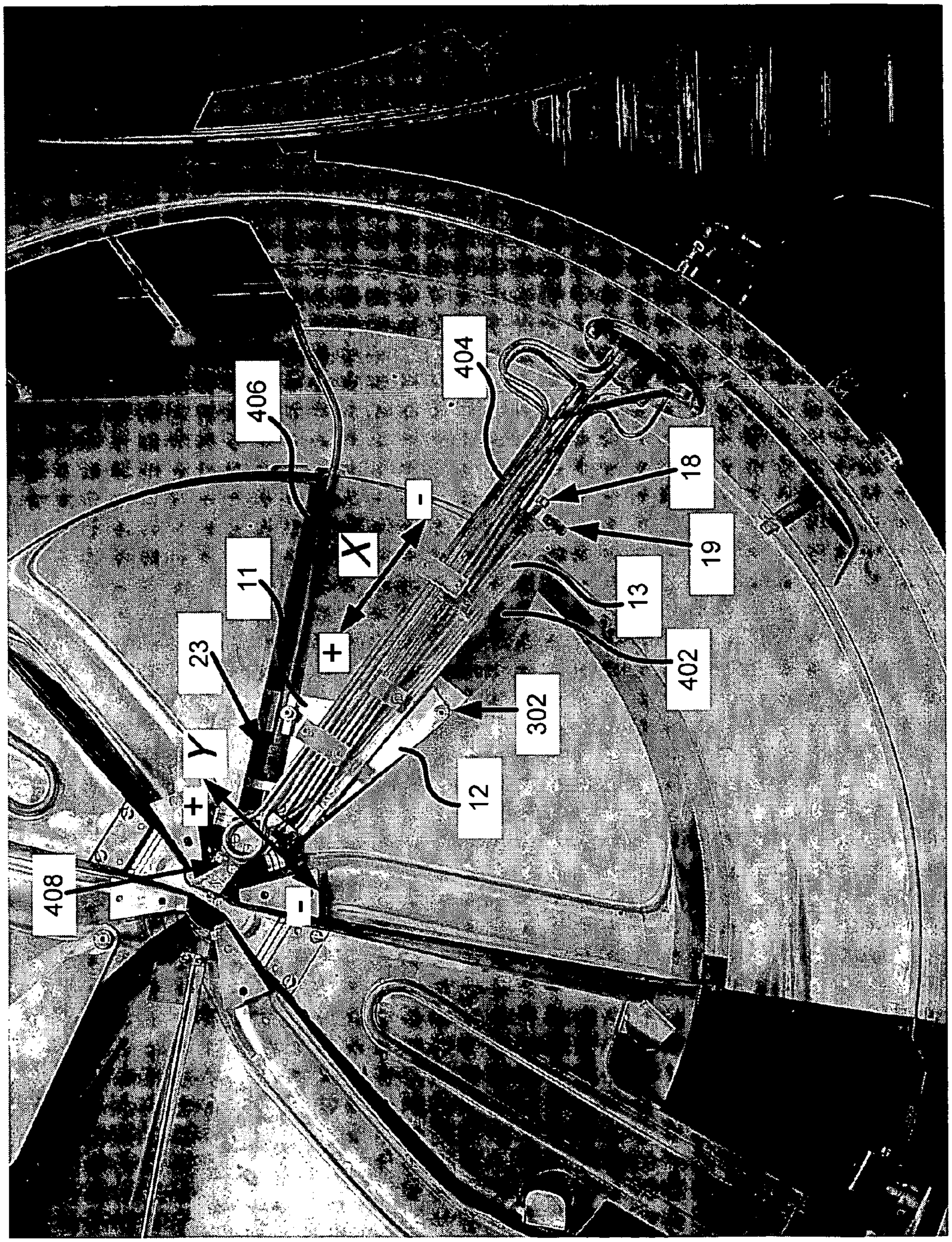
FIG. 5 illustrates the exemplary ion source adjustment tool as installed in a cyclotron according to an embodiment of the invention.

FIG. 5 illustrates the exemplary ion source adjustment tool as installed in a cyclotron according to an embodiment of the invention. FIG. 5 shows a portion of the cyclotron chamber. The exemplary ion source adjustment tool may be installed in a magnet pole valley 402, for example. The installation may be done by attaching the bottom plate 11 to the magnet pole surface. The top plate 13 may be coupled to an ion source assembly 408, particularly an ion source tube (not shown). The pipes 404 may include water-cooling pipes and gas lines for providing plasma-producing gases such as hydrogen. A flexible shaft, hidden in a copper tube 406, may be coupled, via a coupling 23, to the worm gear assembly on one end, and be coupled to a driving unit on the other end outside the cyclotron chamber. The driving unit may comprise a motor for turning the flexible shaft in either direction, thereby causing the worm gear assembly to move the middle plate 12 back and forth in the lateral directions (i.e., ±Y directions). Since the range of movement caused by the worm gear assembly is only a couple of millimeters while the ion source tube is about 50 mm away from the pivot 302, the movement of the ion source tube is effectively a linear motion.

To replace the ion source, the top plate 13, with the old ion source tube attached, may be removed from the chamber. Then, the old ion source tube may be replaced by a new one. An angle tool may be used to facet the slit opening on the new ion source tube in an appropriate angle. Next, the top plate 13, with the new ion source tube attached, may be re-installed in the magnet pole valley 402. Since the stop screw 18 "remembers" the relative position between the top plate 13 and the middle plate 12, such position may be easily restored by tightening the knurled screw 19 until the stop screw 18 touches the middle plate 12. A feeler gauge (not shown) may used to quickly ascertain that the original distance (approximately 1.5 mm, for example) between the puller and the ion source tube has been restored. Once the cyclotron chamber has been closed and pumped down to an acceptable vacuum level, an output of the new ion source may be measured, for example, with an ion probe. Based on the measured output (i.e., the ion probe current), the worm gear assembly may be continuously adjusted from outside the cyclotron chamber to move the middle plate 12 (and thus the top plate 13 and the ion source tube attached thereto) in the ±Y directions, until a desired ion source output is measured. For example, the ion source tube may be initially moved in one direction (e.g., +Y direction). If the ion probe current increases, the ion source tube may be kept moving in the same direction. If the ion probe current starts to drop, that is, it passes a maximum value, the ion source tube may have passed an optimal position. The ion source adjustment tool may control the ion source tube to move in an opposite direction until a maximum value is measured for the ion probe current. Apart from the adjustment upon installation of a new ion source, the optimization may also be performed during operation of the cyclotron.

Since the ion source tube's longitudinal position has been restored upon installation, and the lateral position is remotely and continuously adjustable while the cyclotron chamber is under high vacuum, service time required for the ion source may be significantly shorter than with the traditional approach. As a result, the service engineer(s) may have much less radiation exposure. Due to the faster and easier installation, highly skilled service engineers are no longer necessary for consistent results.

Figure 6:
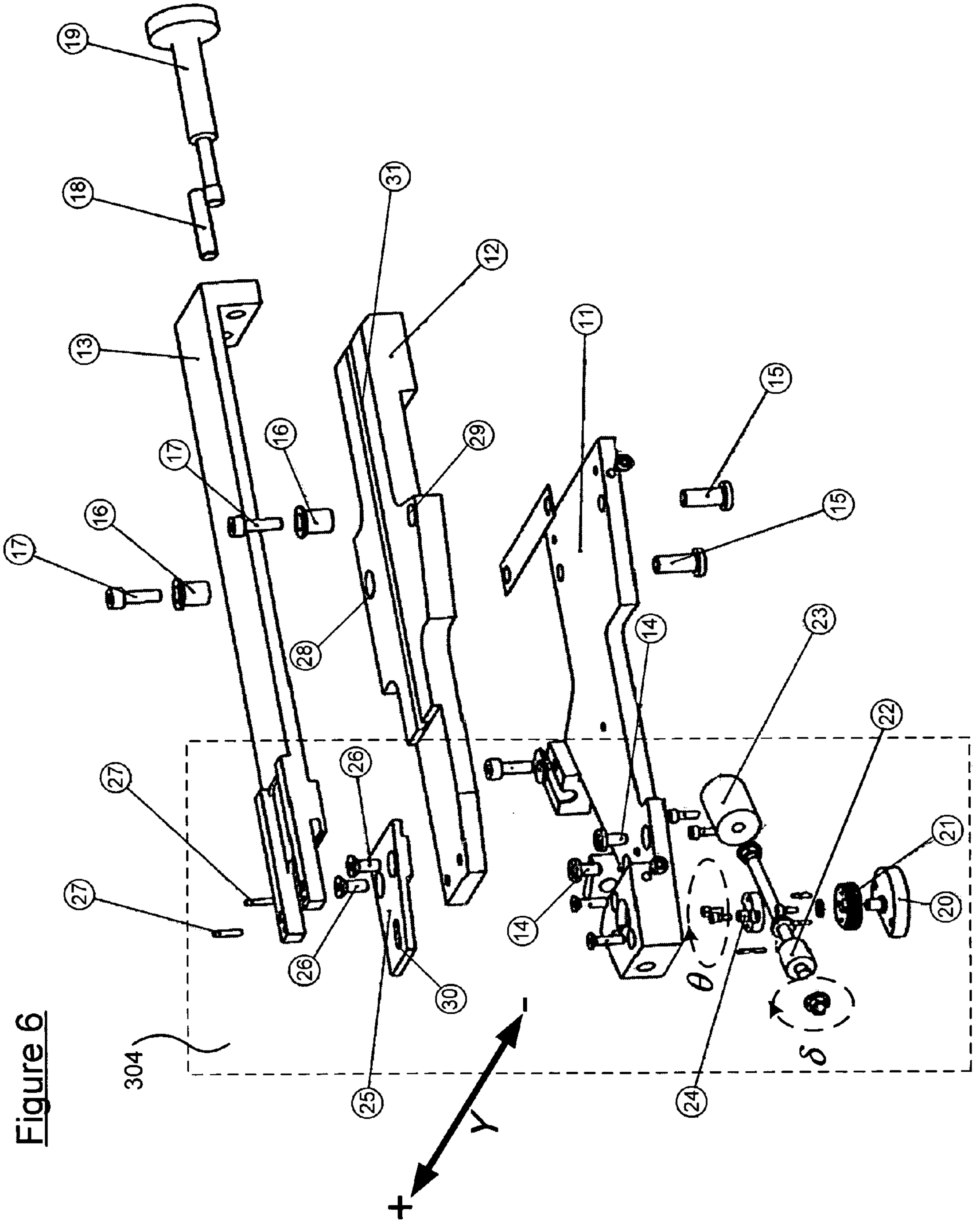
FIG. 6 is a mechanical diagram illustrating various parts of the exemplary ion source adjustment tool.

Referring now to FIG. 6, there is shown a mechanical diagram illustrating various parts of the exemplary ion source adjustment tool. In addition to the top plate 13, the middle plate 12 and the bottom plate 11, the exemplary ion source adjustment tool may comprise screws 14 for fastening the bottom plate 11 to a magnet pole surface inside the cyclotron chamber, for example. Screws 17 may pass through the collars 16 and may be threaded into the nuts 15, so as to fasten the middle plate 12 to the bottom plate 11. Note that the holes 28 and 29, which host the collars 16, are slightly different in size. The hole 28 is slightly larger than the hole 29, thereby allowing a limited rotation of the middle plate 12 around the hole 29. The hole 29 corresponds to the pivot 302 shown in FIGS. 3-5. The worm gear assembly 304 may comprise a base 20 that is attached to the bottom plate 11. The base 20 may comprise a shaft around which a gear 21 may rotate. A worm 22 (driving gear) may be coupled to the gear 21 (driven gear) for causing its rotation. There may be a large gear ratio between the worm 22 and the gear 21. That is, several turns of the worm 22 may cause one turn of the gear 21. Thus, fine adjustment of the gear 21 may be achieved through the worm 22. A shaft component may be attached to and rotate with the gear 21. The shaft component may comprise a shaft 24 that is not aligned with the gear 21's center of rotation. That is, the shaft 24 is intentionally made to be off-centered. The shaft 24 may pass through a track 30 in a plate 25 which is attached to the middle plate 12 with two screws 26. Thus, when the worm 22 is turned (e.g., in the δ-direction), it drives the gear 21, causing the shaft 24 to rotate (e.g., in the θ-direction). As the shaft 24 rotates, it slides in the track 30, causing the middle plate 12 to rotate around the hole 29 (or pivot 302). Since the top plate 13 is coupled to the middle plate 12 by the knurled screw 19 and by two bolts 27, the slight rotation of the middle plate 12 may cause the top plate 13, as well as an ion source tube attached thereto, to move laterally, in the ±Y directions. In operation, the worm 22 is typically coupled to a flexible shaft (not shown) through the coupling 23.

Figure 8:
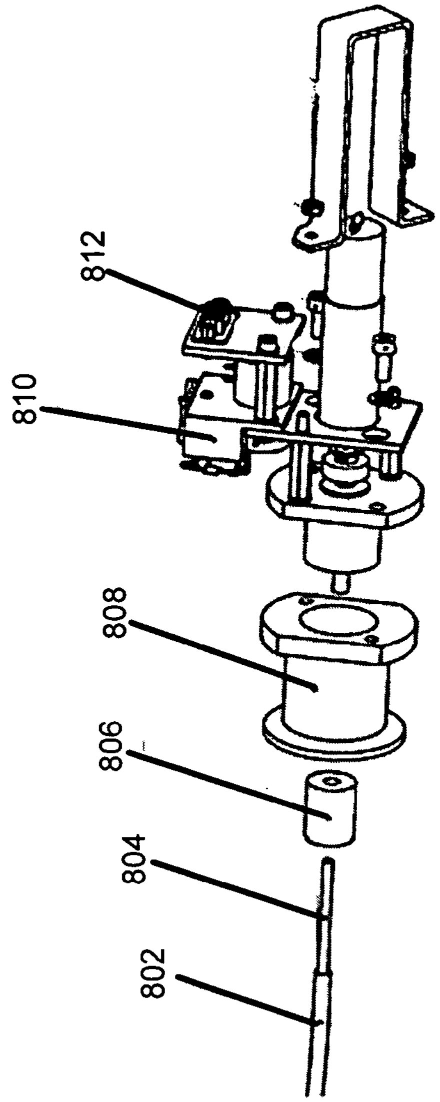
FIG. 8 illustrates various parts of the exemplary driving unit.
Figure 7:
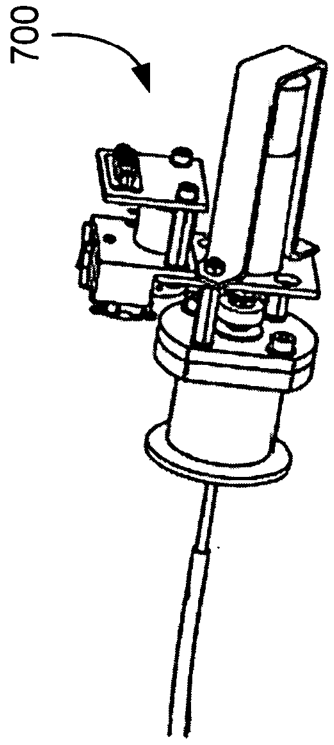
FIG. 7 illustrates an exemplary driving unit for use with the exemplary ion source adjustment tool according to an embodiment of the invention.

The flexible shaft may be coupled to a driving unit located outside the cyclotron chamber. FIG. 7 illustrates an exemplary driving unit 700 for use with the exemplary ion source adjustment tool according to an embodiment of the invention. FIG. 8 illustrates various parts of the exemplary driving unit 700. The exemplary driving unit 700 may comprise a motor assembly 810. A flexible shaft 804, shielded and guided by a copper tube 802, may be coupled to the motor assembly 810 through a coupling 806 and a collar component 808. The motor assembly 810 may further comprise an interface connector 812 to accommodate a connection to a hand control unit.

Figure 9:
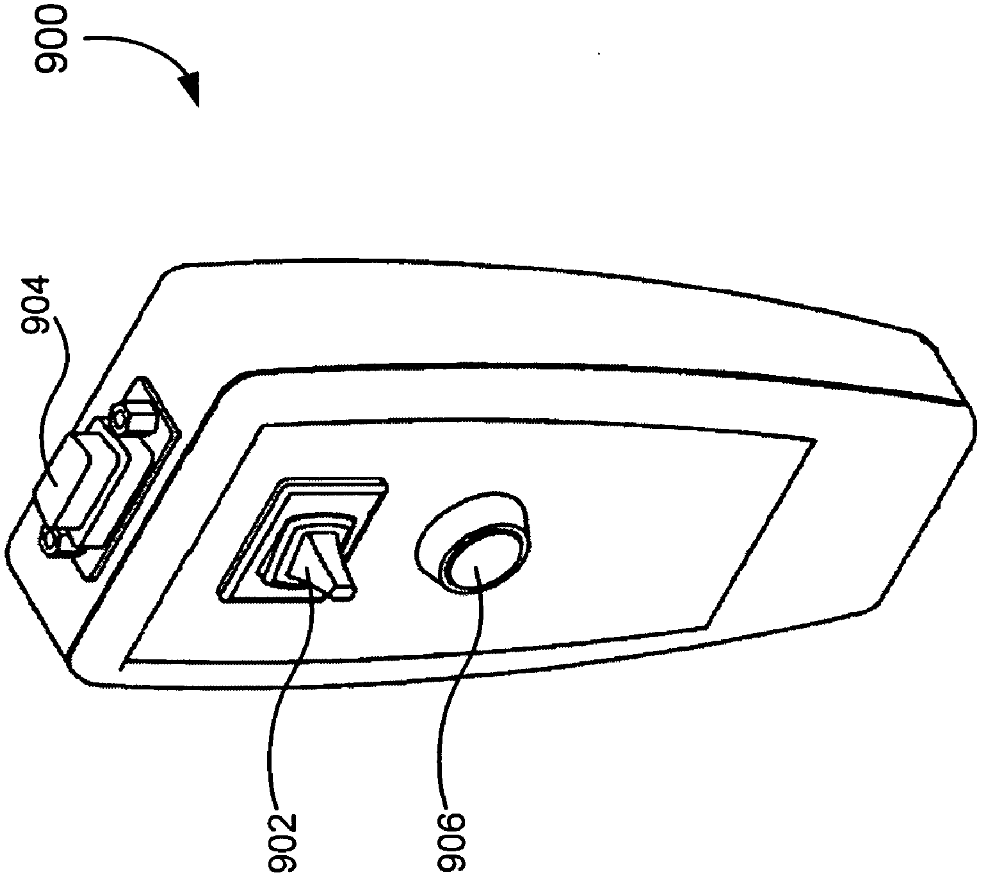
FIG. 9 illustrates an exemplary hand control unit for use with the exemplary driving unit according to an embodiment of the invention.

FIG. 9 illustrates an exemplary hand control unit 900 for use with the exemplary driving unit 700 according to an embodiment of the invention. The exemplary hand control unit 900 may comprise an interface connector 904. A matching cable (e.g., a D-sub cable) may be used to connect the interface connector 904 with the interface connector 812, thereby putting the driving unit 700 within control of the hand control unit 900. The hand control unit 900 may comprise a first switch 902 for causing the driving motor to change its direction of rotation, and a second switch 906 for causing the driving motor to rotate. In operation, after a new ion source tube is positioned with the adjustment tool, the cyclotron chamber may be closed and pumped down. Then, the ion source may be activated and its output measured. The hand control unit 900 may now be used to control the driving unit 700 which in turn drives the worm gear assembly. With the hand control unit 900, the lateral position of the ion source tube may be continuously changed in either direction. This may allow an optimal lateral position to be found that corresponds to a desired output from the ion source.

While the foregoing description includes many details and specificities, it is to be understood that these have been included for purposes of explanation only, and are not to be interpreted as limitations of the present invention. It will be apparent to those skilled in the art that other modifications to the embodiments described above can be made without departing from the spirit and scope of the invention. Accordingly, such modifications are considered within the scope of the invention as intended to be encompassed by the following claims and their legal equivalents.

What is claimed is:

1. An apparatus for ion source positioning and adjustment, the apparatus comprising a bottom plate, a middle plate and a top plate, wherein:

the top plate is coupled to an ion source cube and the middle plate by a first adjustment mechanism for causing the top plate to move in a first direction, wherein the first adjustment mechanism positions the top plate in a predetermined position with respect to the middle plate; and the middle plate is coupled to the bottom plate by a second adjustment mechanism for causing the middle plate to move in a second direction with respect to the bottom plate, wherein the second adjustment mechanism comprises a worm gear assembly having a shaft component that passes an off-centered shaft through part of the middle plate.

2. The apparatus according to claim 1, wherein the first adjustment mechanism comprises a knurled screw and a stop screw, wherein the knurled screw causes the top plate to move in the first direction, and the stop screw stops the top plate in a predetermined position with respect to the middle plate.

3. The apparatus according to claim 1, wherein:

the first adjustment mechanism causes the ion source tube to move in the first direction; and the worm gear assembly causes the ion source tube to move in the second direction.

4. The apparatus according to claim 3, wherein the bottom plate is attached to a part of a cyclotron.

5. The apparatus according to claim 3, wherein the worm gear assembly is driven by a flexible shaft.

6. The apparatus according to claim 1, wherein:

the movement of the top plate in the first direction is a linear movement; and the movement of the middle plate in the second direction is a rotational movement.

7. A method for ion source positioning and adjustment, the method comprising:

coupling an ion source tube to a top plate of an adjustment tool, wherein the top plate is coupled to a middle plate by a first adjustment mechanism for causing the top plate to move in a first direction;

installing the adjustment tool by attaching a bottom plate of the adjustment tool to a chamber of a cyclotron;

adjusting the first adjustment mechanism until the top plate is at a predetermined position with respect to the middle plate; and driving a second adjustment mechanism that causes the middle plate to move in a second direction with respect to the bottom plate, until a desired output of the ion source tube is measured.

8. The method according to claim 7, wherein the first adjustment mechanism comprises a knurled screw and a stop screw, wherein the knurled screw causes the top plate to move in the first direction, and the stop screw stops the top plate in a predetermined position with respect to the middle plate.

9. The method according to claim 7, wherein the second adjustment mechanism comprises a worm gear assembly having a shaft component that passes an off-centered shaft through part of the middle plate.

10. The method according to claim 9, wherein:

the top plate is coupled to an ion source tube;

the first adjustment mechanism causes the ion source tube to move in the first direction; and the worm gear assembly causes the ion source tube to move in the second direction.

11. The method according to claim 10, wherein the bottom plate is attached to a part of a cyclotron.

12. The method according to claim 10, wherein the worm gear assembly is driven by a flexible shaft.

13. The method according to claim 7, wherein:

the movement of the top plate in the first direction is a linear movement; and the movement of the middle plate in the second direction is a rotational movement.

14. A PET tracer production system, the system comprising:

a target comprising atoms of a first type;

an ion source adapted to produce one or more ions;

a particle accelerator capable of accelerating the one or more ions and directing the one or more ions towards the target to change the atoms of the first type to atoms of a second type; and an apparatus for positioning and adjusting the ion source, the apparatus comprising a bottom plate, a middle plate and a top plate, wherein:

the top plate is coupled to the middle plate by a first adjustment mechanism for causing the top plate to move in a first direction, wherein the first adjustment mechanism positions the top plate in a predetermined position with respect to the middle plate; and the middle plate is coupled to the bottom plate by a second adjustment mechanism for causing the middle plate to move in a second direction with respect to the bottom plate.

15. The PET tracer production system according to claim 14, wherein the first adjustment mechanism comprises a knurled screw and a stop screw, wherein the knurled screw causes the top plate to move in the first direction, and the stop screw stops the top plate in a predetermined position with respect to the middle plate.

16. The PET tracer production system according to claim 14, wherein the second adjustment mechanism comprises a worm gear assembly having a shaft component that passes an off-centered shaft through part of the middle plate.

17. The PET tracer production system according to claim 16, wherein:

the top plate is coupled to an ion source tube;

the first adjustment mechanism causes the ion source tube to move in the first direction; and the worm gear assembly causes the ion source tube to move in the second direction.

18. The PET tracer production system according to claim 17, wherein the bottom plate is attached to a part of the particle accelerator.

19. The PET tracer production system according to claim 17, wherein the worm gear assembly is driven by a flexible shaft.

20. The PET tracer production system according to claim 14, wherein:

the movement of the top plate in the first direction is a linear movement; and the movement of the middle plate in the second direction is a rotational movement.

* * * * *